(12) United States Patent
Granger et al.

(10) Patent No.: US 10,201,379 B2
(45) Date of Patent: Feb. 12, 2019

(54) RETAINING SCREW DRIVER ASSEMBLY

(71) Applicant: Biomet Manufacturing, LLC, Warsaw, IN (US)

(72) Inventors: Daren Granger, Warsaw, IN (US); Anthony J Metzinger, Winona Lake, IN (US)

(73) Assignee: Biomet Manufacturing, LLC, Warsaw, IN (US)

(*) Notice: Subject to any disclaimer, the term of this patent is extended or adjusted under 35 U.S.C. 154(b) by 415 days.

(21) Appl. No.: 14/992,275

(22) Filed: Jan. 11, 2016

(65) Prior Publication Data
US 2016/0262818 A1 Sep. 15, 2016

Related U.S. Application Data
(60) Provisional application No. 62/101,708, filed on Jan. 9, 2015.

(51) Int. Cl.
A61B 17/88 (2006.01)
(52) U.S. Cl.
CPC .............................. A61B 17/8888 (2013.01)

(58) Field of Classification Search
CPC ... A61B 17/88; A61B 17/888; A61B 17/8888; A61B 17/8875
See application file for complete search history.

(56) References Cited

U.S. PATENT DOCUMENTS

| 6,565,573 | B1 | 5/2003 | Ferrante | |
|---|---|---|---|---|
| 8,394,103 | B2 | 3/2013 | O'Reilly et al. | |
| 2003/0236529 | A1* | 12/2003 | Shluzas | A61B 17/7079 606/105 |
| 2005/0033307 | A1* | 2/2005 | Cook | A61B 17/888 606/104 |
| 2010/0211115 | A1* | 8/2010 | Tyber | A61B 17/863 606/305 |
| 2012/0253355 | A1* | 10/2012 | Murray | A61B 17/8888 606/104 |
| 2014/0276891 | A1* | 9/2014 | Defalco | A61B 17/8875 606/104 |

* cited by examiner

Primary Examiner — Christopher Beccia
(74) Attorney, Agent, or Firm — Schwegman Lundberg & Woessner, P.A.

(57) ABSTRACT

An apparatus can include a shaft having a mating end and a driving end and having an axial slot; a sliding member located within the axial slot; and an activator to advance the sliding member towards the mating end of the shaft; wherein the axial slot includes a surface proximate the mating end to move a distal end of the sliding member into a retaining position.

18 Claims, 4 Drawing Sheets

RETAINING SCREW DRIVER ASSEMBLY

CLAIM OF PRIORITY

This application claims the benefit of U.S. Provisional Patent Application Ser. No. 62/101,708, filed on Jan. 9, 2015, the benefit of priority of which is claimed hereby, and is incorporated by reference herein in its entirety.

FIELD

The present subject matter relates to a retaining screw driver assembly for use in surgery.

BACKGROUND

Surgeons often require screws or other bone fixation devices when performing a variety of orthopedic procedures. A wide variety of bone screws exist which are adapted to perform specific functions or to be compatible with a specific type of bone tissue or orthopedic implant.

However, the use of bone screws presents certain challenges. For example, bone screws which are not secured to the driver during implantation can slip off and become lost within surrounding muscle tissue. Retrieval of these screws proves difficult when the bone area is surrounded by a large amount of soft tissue.

Accordingly, in performing orthopedic surgery it is desirable for the bone screw to be coupled to a driver to allow attachment of the screw to the driver prior to implantation in the bone, in order to avoid losing the screw in the surrounding soft tissue during the procedure, and to allow release of the screw in a desired manner after implantation. For example, U.S. Pat. No. 8,394,103 discusses retaining screws using internal threads.

OVERVIEW

In Example 1, an apparatus includes a shaft having a mating end and a driving end and having an axial slot; a sliding member located within the axial slot; and an activator to advance the sliding member towards the mating end of the shaft; wherein the axial slot includes a surface proximate the mating end to move a distal end of the sliding member into a retaining position.

In Example 2, the apparatus of Example 1 can optionally include the activator including an internally threaded knob to engage threads on a proximate end of the sliding member.

In Example 3, the apparatus of Example 1 can optionally include a second slot on the shaft.

In Example 4, the apparatus of Example 3 can optionally include a cross-pin located within the second slot to retain the sliding member within the axial slot and prevent rotation of the sliding member as the sliding member is advance down the axial slot.

In Example 5, the apparatus of Example 4 can optionally include the second slot including a J-slot.

In Example 6, the apparatus of Example 1 can optionally include the driving end of the shaft including a mating section to attach to a handle, drill, or other driving member.

In Example 7, the apparatus of Example 1 can optionally include the mating end of the shaft including a shape to mate with a head of a screw.

In Example 8, the apparatus of Example 7 can optionally include the shape being hexagonal.

In Example 9, the Example of Example 1 can optionally include the distal end of the sliding member being thinner than a main body of the sliding member.

In Example 10, the apparatus of Example 1 can optionally include the surface proximate the mating end including a ramp.

In Example 11, the apparatus of Example 10 can optionally include the retaining position of the sliding member including the distal end of the sliding member being raised up by the ramp so as to be at or above an outer surface of the mating end of the shaft to frictionally engage with an inner surface in a head of a bone fixation device.

In Example 12, the apparatus of Example 1 can optionally include the driving end of the shaft being attached to a driving member before or after a bone fixation device is attached to the mating end.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
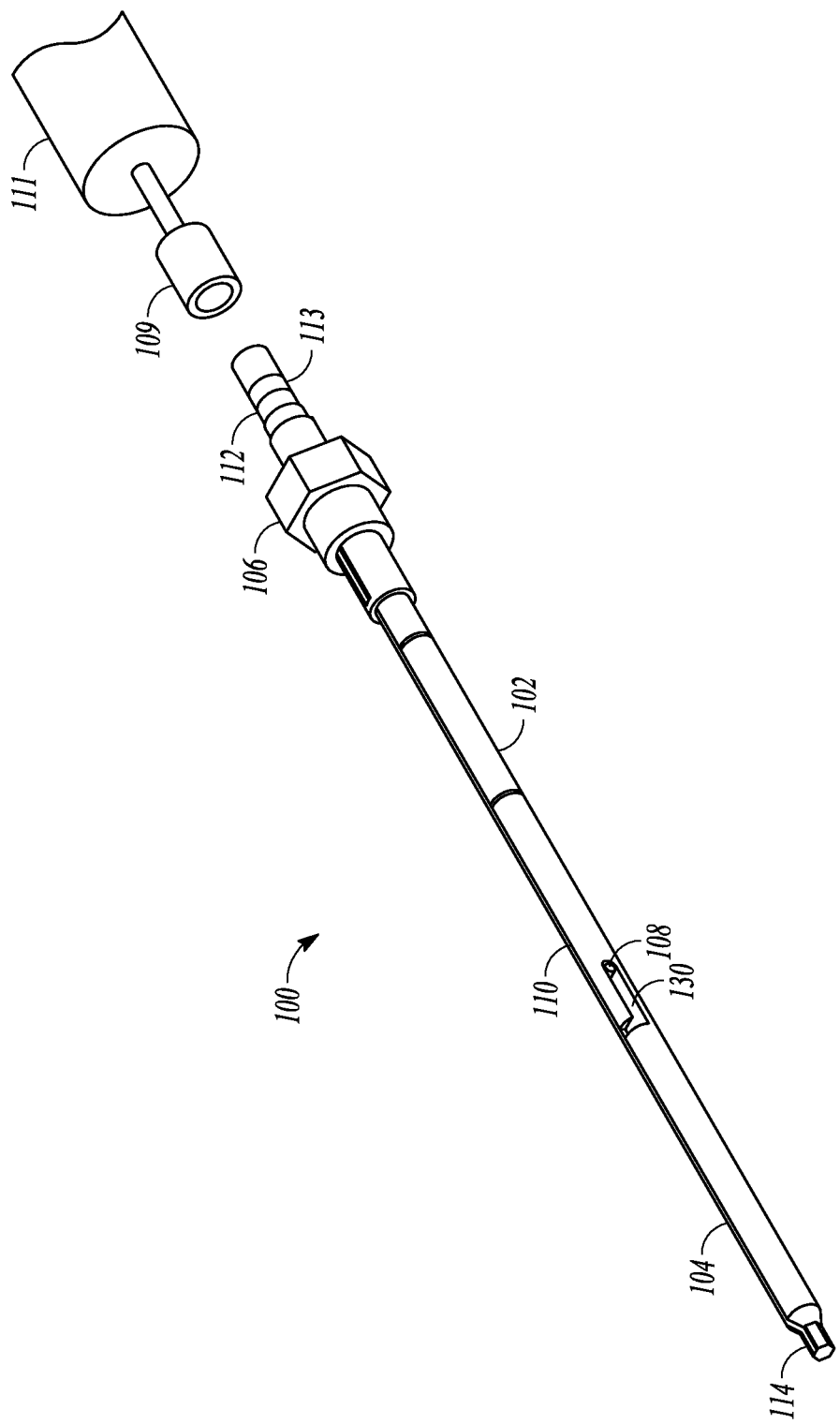
FIG. 1 shows a perspective view of an inserter, in accordance with one embodiment.
Figure 2:
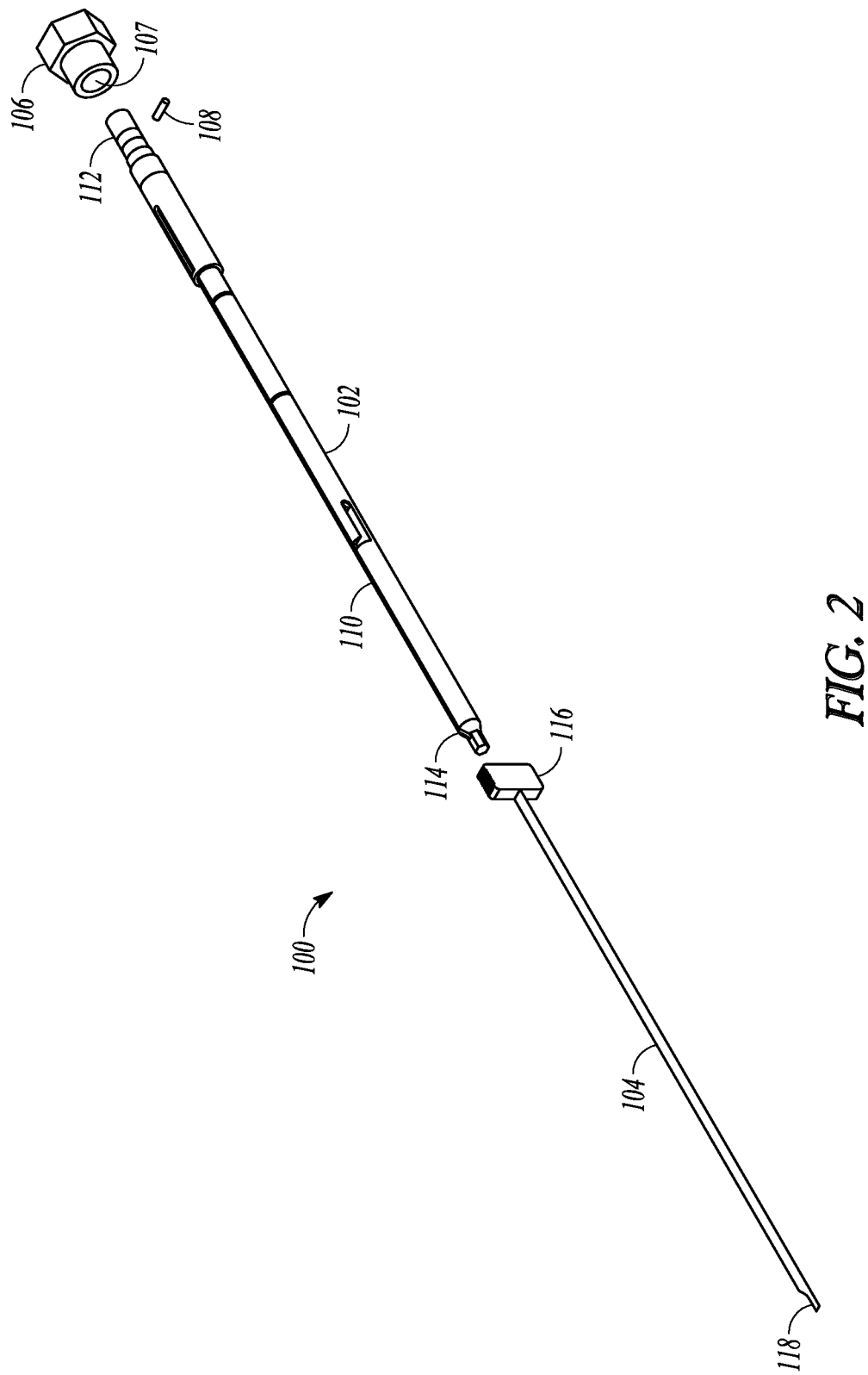
FIG. 2 shows an exploded perspective view of the inserter of FIG. 1.

FIG. 1 shows a perspective view of an inserter 100, in accordance with one embodiment. FIG. 2 shows an exploded perspective view of the inserter 100. In general, the inserter includes a shaft 102, a sliding member 104, an activator, such as a knob 106, and a cross-pin 108.

The shaft 102 includes a mating end 114 and a driving end 112. The mating end 114 of the shaft 102 includes a shape to mate with a head of a bone fixation device, such as a screw. In some non-limiting examples, the shape can be hexagonal, some other polygon shape, a circle, or a blade. The driving end 112 of the shaft includes a mating section 113 to attach to a handle, drill, or other driving member 111. For example, the mating section 113 can be machined to attach to a coupler 109 of the driving member 111 with a Hudson, Jacobs, AO, or Stryker Hall quick-connect feature, for example.

The shaft includes an axial slot 110 running along the outer surface of the shaft 110 to the mating end 114 of the shaft. The sliding member 104 is located within the axial slot 110. The knob 106 engages the sliding member 104 to advance the sliding member 104 towards the mating end 114 of the shaft 110.

Figure 3:
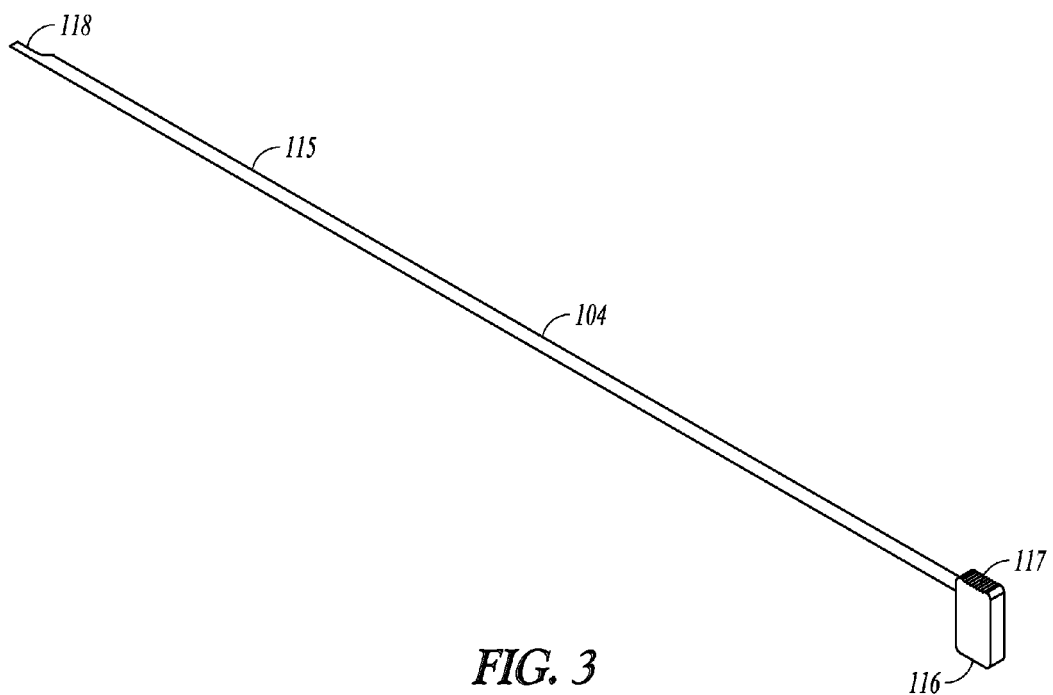
FIG. 3 shows a perspective view of a sliding member, in accordance with one embodiment.

Referring also to FIG. 3, which shows a perspective view of the sliding member 104, in accordance with one embodiment. The sliding member 104 includes a main body 115 which is shaped to fit within the slot 110 of the shaft 102, and a thinner distal end 118 which is the portion of the sliding member 104 that frictionally engages with the head of a bone fixation device to retain the device, as will be explained further below. The sliding member 104 can include a proximate end 116 that engages with the activator 106. In one example, the end 116 can include external threads 117 that engage with internal threads 107 on the knob 106, such that rotating the knob 106 advances the sliding member 104 down the axial slot 110.

Figure 4:
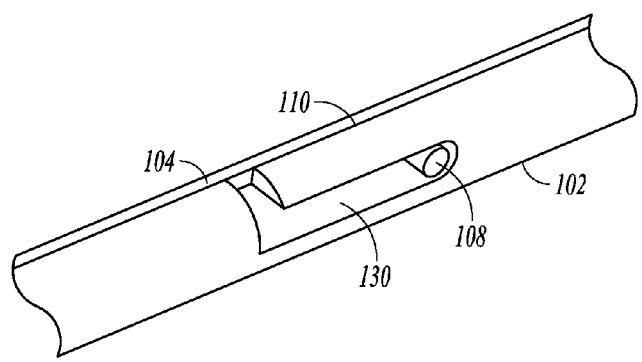
FIG. 4 shows a view of a slot in the shaft of the inserter, in accordance with one embodiment.

In one embodiment, the shaft 102 includes a second slot 130 also running axially along the shaft 102. Referring also to FIG. 4, which shows a detailed view of the slot 130 in the shaft 102 of the inserter, the second slot 130 opens into the axial slot 110. In one embodiment, the second slot 130 can be a J-slot. The cross-pin 108 is located within the second slot 130 to retain the sliding member 104 within the axial slot 110 and prevent rotation of the sliding member 104 as the sliding member 104 is advance down the axial slot 110.

Figure 5:
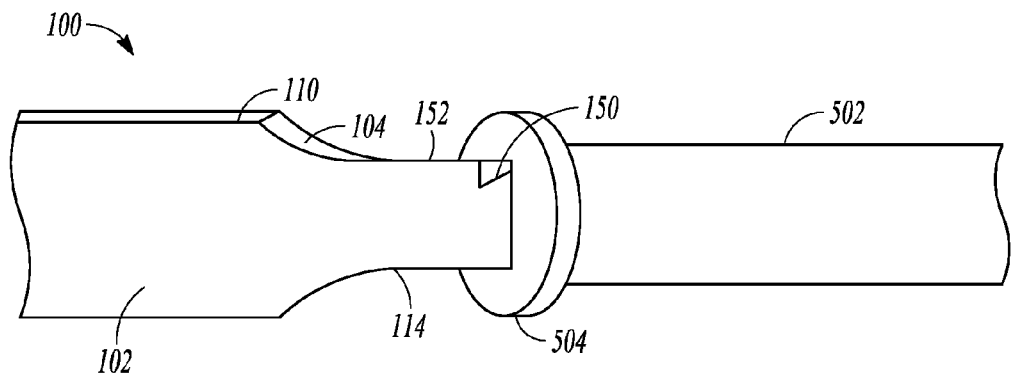
FIG. 5 shows the inserter retaining a bone fixation device, in accordance with one embodiment.
Figure 6:
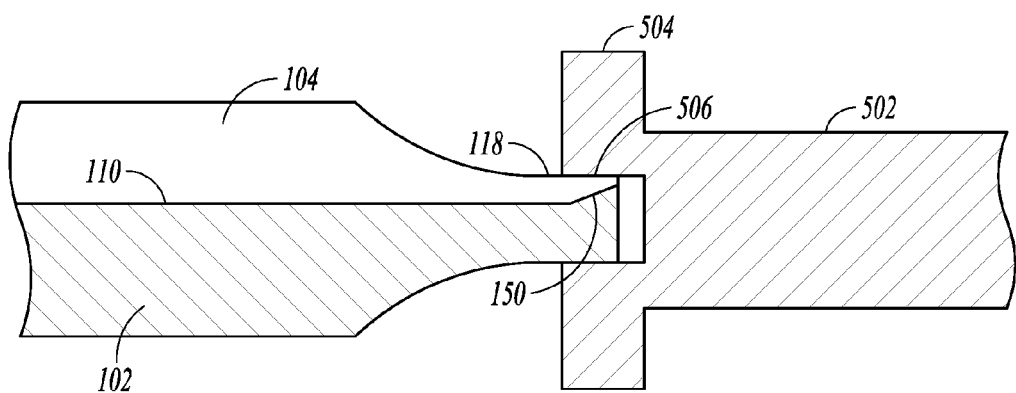
FIG. 6 shows a side, cross-section view of the inserter retaining a bone fixation device.

Referring now also to FIGS. 5 and 6 which show a side view and a cross-section side view of the inserter 100 retaining a bone fixation device 502, the axial slot 110 includes a surface proximate the mating end 114 of the shaft 102 shaped to move the distal end 118 of the sliding member into a retaining position. In one example, the surface includes a ramp 150. When the inserter 100 is in the retaining position, the distal end 118 of the sliding member 104 is raised up by the ramp 150 so as to be at or above an outer surface 152 of the mating end 114 of the shaft 110 to frictionally engage with an inner surface 506 in a head 504 of the bone fixation device 502.

To assemble the inserter 100, the sliding member 104 is placed into the axial slot 110 of the shaft 102. The sliding member 104 is pinned in place by the cross-pin 108 engaging the sliding member 104 through the second slot 130.

In use, the mating end 114 of the shaft 102 is inserted within the head 504 of the bone fixation device 502. By turning knob 106 the sliding member is advanced down the axial slot 110 toward the mating end 114 of the shaft 102. When the distal end 118 of the sliding member 104 reaches the ramp 150 of the slot 110, the tip of the distal end 118 is deflected and raised via the ramp 150 to create a friction force against the inner surface of the head 504 of the bone fixation device 502, and thus retain the bone fixation device 502 on the mating end 114 of the shaft 102. By using frictional engagement and not requiring specific mating features, the present inserter 100 can be used with multiple different types of screws having varying head mating features.

Either before or after the bone fixation device 502 is attached to the mating end 114, the driving end 112 of the shaft 102 can be attached to a driving member, such as a handle, drill, or other driving device. The present inserter 100 allows for retention of the bone fixation device to the driver and in addition allows the driver to connect to a drill. Moreover, the use of the axial slot permits for a solid core shaft.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The claimed invention is:

1. An apparatus comprising:
a shaft having a mating end and a driving end and having an axial slot and a second slot extending from the axial slot;
a sliding member located within the axial slot; and
an activator to advance the sliding member towards the mating end of the shaft; and
a cross-pin located within the second slot to retain the sliding member within the axial slot and prevent rotation of the sliding member as the sliding member is advance down the axial slot;
wherein the axial slot includes a surface proximate the mating end to move a distal end of the sliding member into a retaining position.

2. The apparatus of claim 1, wherein the activator includes an internally threaded knob to engage threads on a proximate end of the sliding member.

3. The apparatus of claim 1, wherein the second slot includes a J-slot.

4. The apparatus of claim 1, wherein the driving end of the shaft includes a mating section to attach to a handle, drill, or other driving member.

5. The apparatus of claim 1, wherein the mating end of the shaft includes a shape to mate with a head of a screw.

6. The apparatus of claim 5, wherein the shape is hexagonal.

7. The apparatus of claim 1, wherein the distal end of the sliding member is thinner than a main body of the sliding member.

8. The apparatus of claim 1, wherein the surface proximate the mating end includes a ramp.

9. The apparatus of claim 8, wherein the retaining position of the sliding member includes the distal end of the sliding member being raised up by the ramp so as to be at or above an outer surface of the mating end of the shaft to frictionally engage with an inner surface in a head of a bone fixation device.

10. The apparatus of claim 1, wherein the driving end of the shaft can be attached to a driving member before or after a bone fixation device is attached to the mating end.

11. An apparatus comprising:
    a shaft having a mating end and a driving end and having an axial slot and having a second slot;
    a sliding member located within the axial slot;
    a cross-pin located within the second slot to retain the sliding member within the axial slot and prevent rotation of the sliding member as the sliding member is advance down the axial slot; and
    an activator to advance the sliding member towards the mating end of the shaft;
    wherein the axial slot includes a ramp proximate the mating end to raise a distal end of the sliding member up to or above an outer surface of the mating end of the shaft to frictionally engage with an inner surface in a head of a bone fixation device.

12. The apparatus of claim 11, wherein the activator includes a threaded knob to engage threads on a proximate end of the sliding member.

13. The apparatus of claim 11, wherein the second slot includes a J-slot.

14. The apparatus of claim 11, wherein the driving end of the shaft includes a mating section to attach to a handle, drill, or other driving member.

15. The apparatus of claim 11, wherein mating end of the shaft includes a shape to mate with a head of a screw.

16. A method comprising:
    placing a mating end of a shaft of an inserter within a head of a bone fixation device;
    advancing a sliding member located within an axial slot on the shaft down the axial shaft toward a distal end of the shaft, wherein there is a cross-pin located within a second slot extending from the axial slot to retain the sliding member within the axial slot and prevent rotation of the sliding member as the sliding member is advance down the axial slot; and
    frictionally engaging an inners surface of the head of the bone fixation device with a distal end of the sliding member to retain the bone fixation device on the mating end of the shaft.

17. The method of claim 16, wherein the axial slot includes a ramp proximate the mating end to raise a distal end of the sliding member into a retaining position.

18. The method of claim 16, including a threaded knob on the shaft to engage threads on a proximate end of the sliding member to advance the sliding member within the axial slot.

* * * * *